US012672789B2

(12) United States Patent (10) Patent No.: US 12,672,789 B2

Tamura (45) Date of Patent: Jul. 7, 2026

---

(54) BIOLOGICAL CONDITION MEASUREMENT APPARATUS, BIOLOGICAL CONDITION MEASUREMENT METHOD AND BIOLOGICAL CONDITION MEASUREMENT SYSTEM

(71) Applicant: FINGGAL LINK CO., LTD., Tokyo (JP)

(72) Inventor: Yasuhiro Tamura, Tokyo (JP)

(73) Assignee: FINGGAL LINK CO., LTD., Tokyo (JP)

( * ) Notice: Subject to any disclaimer, the term of this patent is extended or adjusted under 35 U.S.C. 154(b) by 267 days.

(21) Appl. No.: 18/498,039

(22) Filed: Oct. 31, 2023

(65) Prior Publication Data

US 2024/0057884 A1 Feb. 22, 2024

Related U.S. Application Data

(63) Continuation of application No. PCT/JP2022/018744, filed on Apr. 25, 2022.

(30) Foreign Application Priority Data

May 7, 2021 (JP) ................................. 2021-078982

(51) Int. Cl.
*A61B 5/05* (2021.01)
*A61B 5/00* (2006.01)

(52) U.S. Cl.
CPC .............. *A61B 5/05* (2013.01); *A61B 5/7264* (2013.01)

(58) Field of Classification Search
None
See application file for complete search history.

(56) References Cited

U.S. PATENT DOCUMENTS

2016/0338652 A1 11/2016 Yoshioka et al.
2019/0391249 A1 12/2019 Takeuchi et al.
(Continued)

FOREIGN PATENT DOCUMENTS

EP 3967215 A1 * 3/2022 ............... A61B 5/08
JP 2013242237 A 12/2013
(Continued)

OTHER PUBLICATIONS

Fengyu Wang et al., "ViMo: Multiperson Vital Sign Monitoring Using Commodity Millimeter-Wave Radio", IEEE Internet of Things Journal, Feb. 1, 2021, p. 1294-p. 1307, vol. 8, No. 3, Ieee, USA, 14pp.

*Primary Examiner* — Katherine L Fernandez
(74) *Attorney, Agent, or Firm* — HAUPTMAN HAM, LLP

(57) ABSTRACT

A biological condition measurement apparatus has: a transmitting section that transmits a transmission signal in a frequency band equal to or higher than a millimeter wave band at predetermined time intervals; a receiving section that receives a plurality of reflection signals generated by reflection of the transmission signal on a plurality of measurement subjects; a measuring section that measures a plurality of times of flight from the transmission of the transmission signal by the transmitting section until the reception of the plurality of reflection signals by the receiving section; and an identifying section that identifies a biological condition of each of a plurality of the measurement subjects on the basis of a mode of change of times of flight represented by a plurality of pieces of time-of-flight data representing times of flight that fluctuate in a time range equal to or lower than a first threshold.

18 Claims, 8 Drawing Sheets

(56)     References Cited

U.S. PATENT DOCUMENTS

| | | | |
|---|---|---|---|
| 2020/0268257 A1 | 8/2020 | Wu et al. | |
| 2021/0045697 A1* | 2/2021 | Wang et al. | |
| 2021/0080557 A1* | 3/2021 | Vaishnav | G01S 13/72 |
| 2021/0398666 A1* | 12/2021 | Maslik | A61B 5/4842 |
| 2022/0381877 A1 | 12/2022 | Kim | |
| 2024/0034325 A1* | 2/2024 | Fujinami | B60W 50/14 |

FOREIGN PATENT DOCUMENTS

| | | | | |
|---|---|---|---|---|
| JP | 2016214876 A | 12/2016 | | |
| JP | 2016540960 A | 12/2016 | | |
| JP | 2017161368 A | 9/2017 | | |
| JP | 2021027993 A | 2/2021 | | |
| KR | 10-2122758 B1 | 6/2020 | | |
| WO | WO-2015102713 A2 * | 7/2015 | | G01S 5/14 |

* cited by examiner

TIME OF FLIGHT

TIME

BIOLOGICAL CONDITION MEASUREMENT APPARATUS, BIOLOGICAL CONDITION MEASUREMENT METHOD AND BIOLOGICAL CONDITION MEASUREMENT SYSTEM

CROSS-REFERENCE TO RELATED APPLICATIONS

The present application is a continuation application of International Application number PCT/JP2022/018744, filed on Apr. 25, 2022, which claims priority under 35 U.S.C. § 119(a) to Japanese Patent Application No. 2021-078982, filed on May 7, 2021, contents of which are incorporated herein by reference in their entirety.

BACKGROUND OF THE INVENTION

The present invention relates to a biological condition measurement apparatus, a biological condition measurement method, and a biological condition measurement system for measuring biological conditions of humans.

As disclosed in Japanese Patent Application Publication No. 2016-214876, there are conventionally known methods of measuring heart rates by transmitting millimeter wave signals, and analyzing reflected wave signals generated by the reflection of the transmitted millimeter wave signals on a human body.

In a case where the conventional methods are used, there has been a disadvantage that, if a plurality of humans are in an area toward which millimeter wave signals are transmitted, reflected wave signals are generated from the plurality of humans undesirably, resulting in the deterioration of the precision of measurement of heart rates undesirably.

BRIEF SUMMARY OF THE INVENTION

Therefore, the present invention has been made in view of these matters, and an object thereof is to make it possible to measure biological conditions such as heart rates or respiratory rates even in a case where there are a plurality of humans in an area toward which radio waves are transmitted.

A biological condition measurement apparatus of a first aspect of the present invention has: a transmitting section that transmits a transmission signal in a frequency band equal to or higher than a millimeter wave band at predetermined time intervals; a receiving section that receives a plurality of reflection signals generated by reflection of the transmission signal on a plurality of measurement subjects; a measuring section that measures a plurality of times of flight from the transmission of the transmission signal by the transmitting section until the reception of the plurality of reflection signals by the receiving section; and an identifying section that classifies a plurality of pieces of time-of-flight data representing the plurality of times of flight into a plurality of pieces of time series data including a plurality of pieces of time-of-flight data representing times of flight that fluctuate in a time range equal to or lower than a first threshold, and identifies a biological condition representing motions of an organ of each of a plurality of the measurement subjects on a basis of a mode of change of times of flight represented by each of the plurality of pieces of time series data.

A biological condition measurement method of a second aspect of the present invention has, as steps to be executed by a computer: a step of transmitting a transmission signal in a frequency band equal to or higher than a millimeter wave band at predetermined time intervals; a step of receiving a plurality of reflection signals generated by reflection of the transmission signal on a plurality of measurement subjects; a step of measuring a plurality of times of flight from the transmission of the transmission signal until the reception of the reflection signals; and a step of classifying a plurality of pieces of time-of-flight data representing the plurality of times of flight into a plurality of pieces of time series data including a plurality of pieces of time-of-flight data representing times of flight that fluctuate in a time range equal to or lower than a first threshold, and identifying a biological condition representing motions of an organ of each of a plurality of the measurement subjects on a basis of a mode of change of times of flight represented by each of the plurality of pieces of time series data.

A biological condition measurement system of a third aspect of the present invention includes: a biological condition measurement apparatus; and an information processing apparatus that can communicate with the biological condition measurement apparatus, in which the biological condition measurement apparatus has: a transmitting section that transmits a transmission signal in a frequency band equal to or higher than a millimeter wave band at predetermined time intervals; and a receiving section that receives a plurality of reflection signals generated by reflection of the transmission signal on a plurality of measurement subjects, and either the biological condition measurement apparatus or the information processing apparatus has: a measuring section that measures a plurality of times of flight from the transmission of the transmission signal by the transmitting section until the reception of the plurality of reflection signals by the receiving section; and an identifying section that classifies a plurality of pieces of time-of-flight data representing the plurality of times of flight into a plurality of pieces of time series data including a plurality of pieces of time-of-flight data representing times of flight that fluctuate in a time range equal to or lower than a first threshold, and identifies a biological condition representing motions of an organ of each of a plurality of the measurement subjects on a basis of a mode of change of times of flight represented by each of the plurality of pieces of time series data.

DETAILED DESCRIPTION OF THE INVENTION

Hereinafter, the present disclosure will be described through exemplary embodiments, but the following exemplary embodiments do not limit the invention according to the claims, and not all of the combinations of features described in the exemplary embodiments are necessarily essential to the solution means of the invention.

[Overview of Biological Condition Measurement System S]

Figure 1:
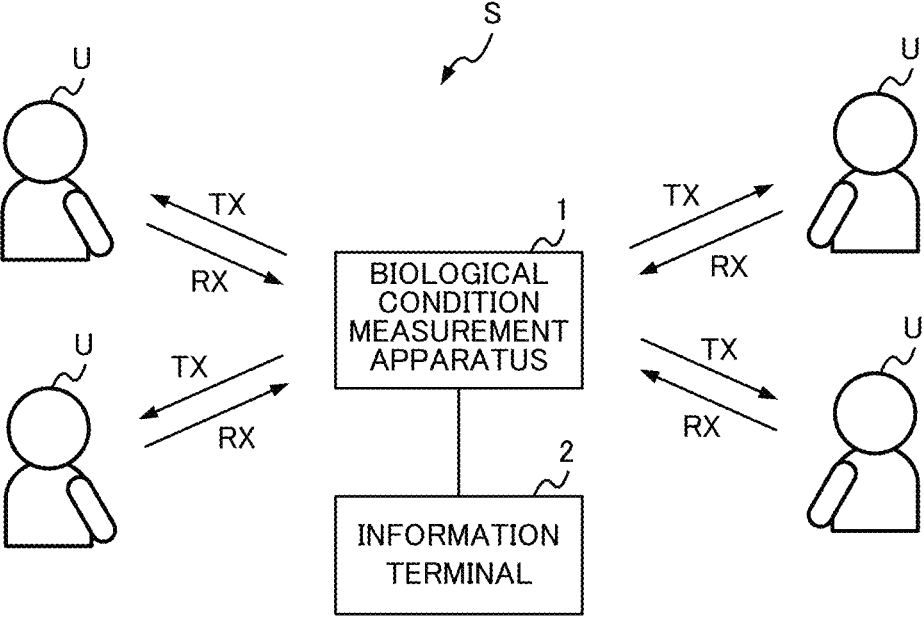
FIG. 1 is a figure depicting an overview of a biological condition measurement system S.

FIG. 1 is a figure depicting an overview of a biological condition measurement system S. The biological condition measurement system S is a system for measuring biological conditions of humans. The biological conditions are heart rates or respiratory rates, or motions of physical parts of humans, and, for example, are represented by change amounts per unit time of the heart rates, the respiratory rates or the motions.

The biological condition measurement system S includes a biological condition measurement apparatus 1 and an information terminal 2. The biological condition measurement apparatus 1 can measure biological conditions of a plurality of humans (measurement subjects U in FIG. 1) within an area where radio waves generated by the biological condition measurement apparatus 1 can reach. The information terminal 2 is a terminal for displaying results of measurement by the biological condition measurement apparatus 1, controlling the biological condition measurement apparatus 1, and so on, and is a computer, a tablet or a smartphone, for example.

The biological condition measurement apparatus 1 transmits, as a transmission signal, radio waves with frequencies equal to or higher than the millimeter wave band in a plurality of directions, and receives reflection signals generated by the reflection of the transmitted radio waves on nearby objects. The biological condition measurement apparatus 1 identifies the distances to the objects having reflected the transmission signal on the basis of the times of flight from the transmission of the transmission signal until the reception of the reflection signal. A human body has tissues that easily reflect radio waves and tissues that do not easily reflect radio waves, and, by identifying the distance to a tissue that easily reflects radio waves, the biological condition measurement apparatus 1 can identify motions of the tissue. For example, the biological condition measurement apparatus 1 measures heart rates by identifying cardiac motions, and measures respiratory rates by identifying pleural motions.

For example, the biological condition measurement apparatus 1 transmits, as a transmission signal, a chirp signal with frequencies that change with time. In a case where the biological condition measurement apparatus 1 transmits a chirp signal, the biological condition measurement apparatus 1 transforms a reflection signal into a frequency-domain signal by the Fourier transform, and identifies a frequency included in the reflection signal. Thereby, the biological condition measurement apparatus 1 can measure the time of flight from the transmission of a signal with the frequency until reception of the signal highly precisely.

[Display Screen of Measurement Results]

Figure 2:
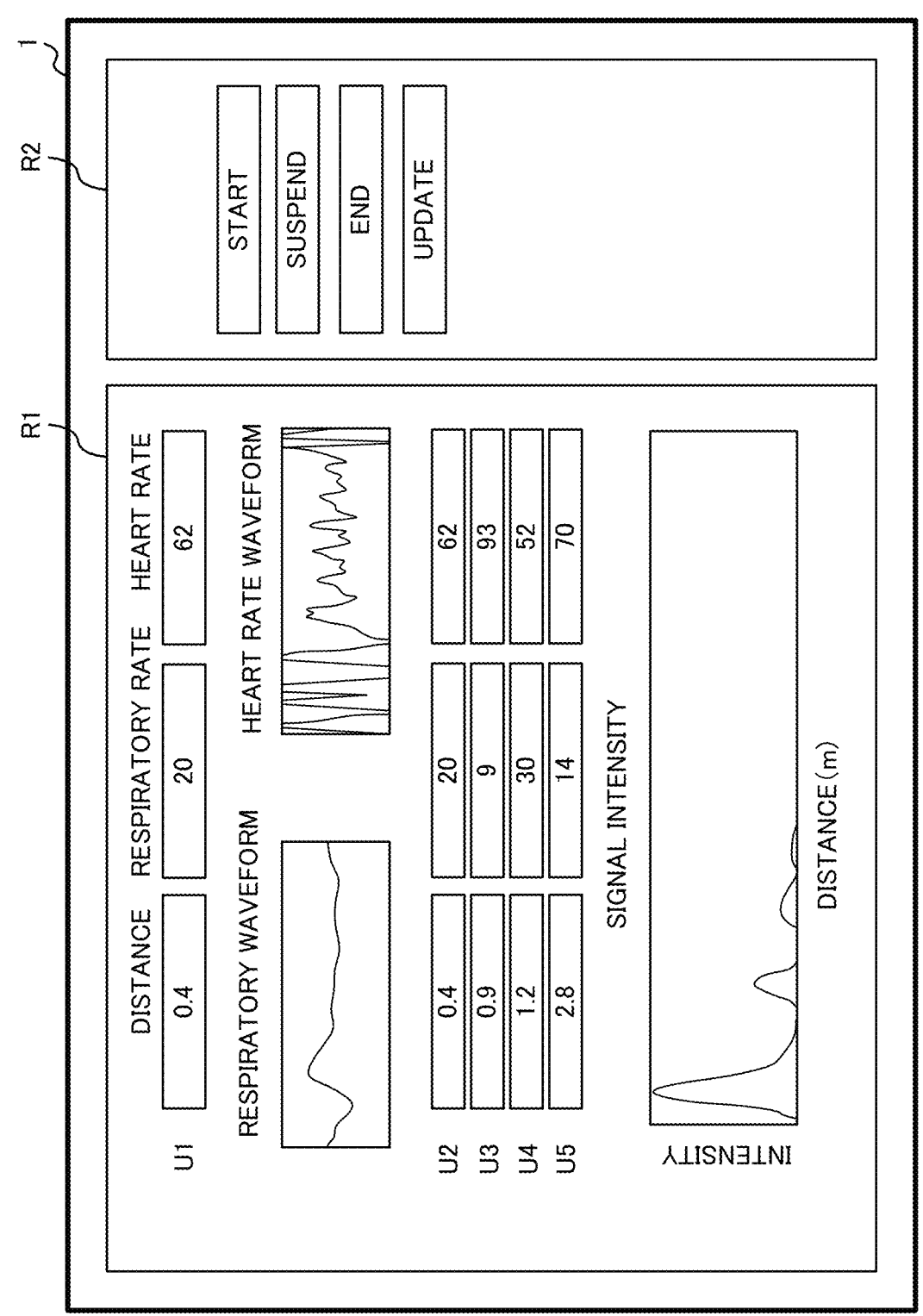
FIG. 2 is a figure depicting an example of a screen representing measurement results displayed on an information terminal 2.

FIG. 2 is a figure depicting an example of a screen representing measurement results displayed on the information terminal 2. The screen depicted in FIG. 2 includes a measurement result display region R1 and a operation region R2.

In the top portion of the region R1, the distance to a measurement subject U1 who is the closest to the biological condition measurement apparatus 1, and the respiratory rate and the heart rate of the measurement subject U1 are depicted. In addition, the respiratory waveform and the heart rate waveform of the measurement subject U1 also are depicted. Below the respiratory waveform and the heart rate waveform, the distances to a plurality of other measurement subjects U, and the respiratory rates and the heart rates of the measurement subjects U are depicted in association with the respective measurement subjects U. Furthermore, in the region R1, a figure depicting the relationship between the distances to the measurement subjects U and the intensities of received reflection signals also is depicted.

In the region R2, images of operation buttons for accepting operation for starting, suspending and ending measurement are displayed. An "update" button in the region R2 is a button for updating measurement results being displayed in the region R1 to the latest measurement results.

Figure 3:
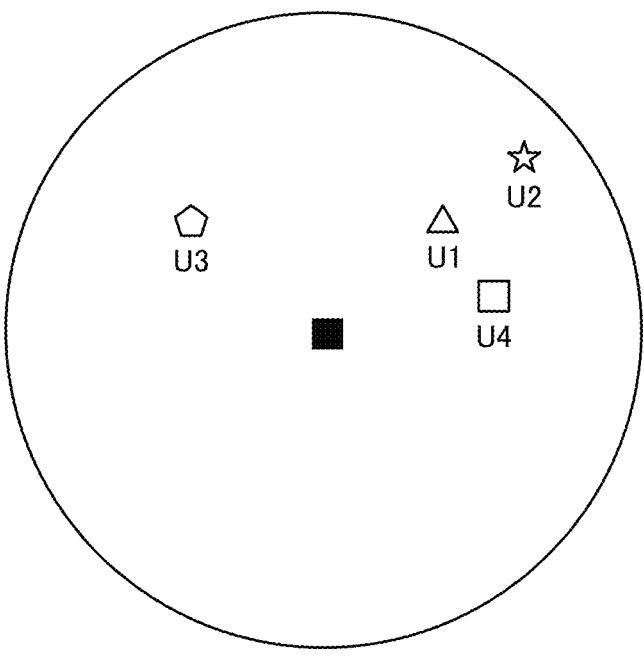
FIG. 3 is a figure depicting another example of a screen representing measurement results displayed on the information terminal 2.

FIG. 3 is a figure depicting another example of a screen representing measurement results displayed on the information terminal 2. FIG. 3 is a figure depicting the positions of a plurality of the measurement subjects U whose biological conditions were measured. A black quadrilateral in FIG. 3 represents the position of the biological condition measurement apparatus 1, and other white figures represent the positions of the plurality of measurement subjects U having reflected the transmission signal. The biological condition measurement apparatus 1 may include the image depicted in FIG. 3 in the screen depicted in FIG. 2 or may cause the information terminal 2 to display the image depicted in FIG. 3 in a case where predetermined operation is performed on the screen depicted in FIG. 2.

[Configuration of Biological Condition Measurement Apparatus 1]

Figure 4:
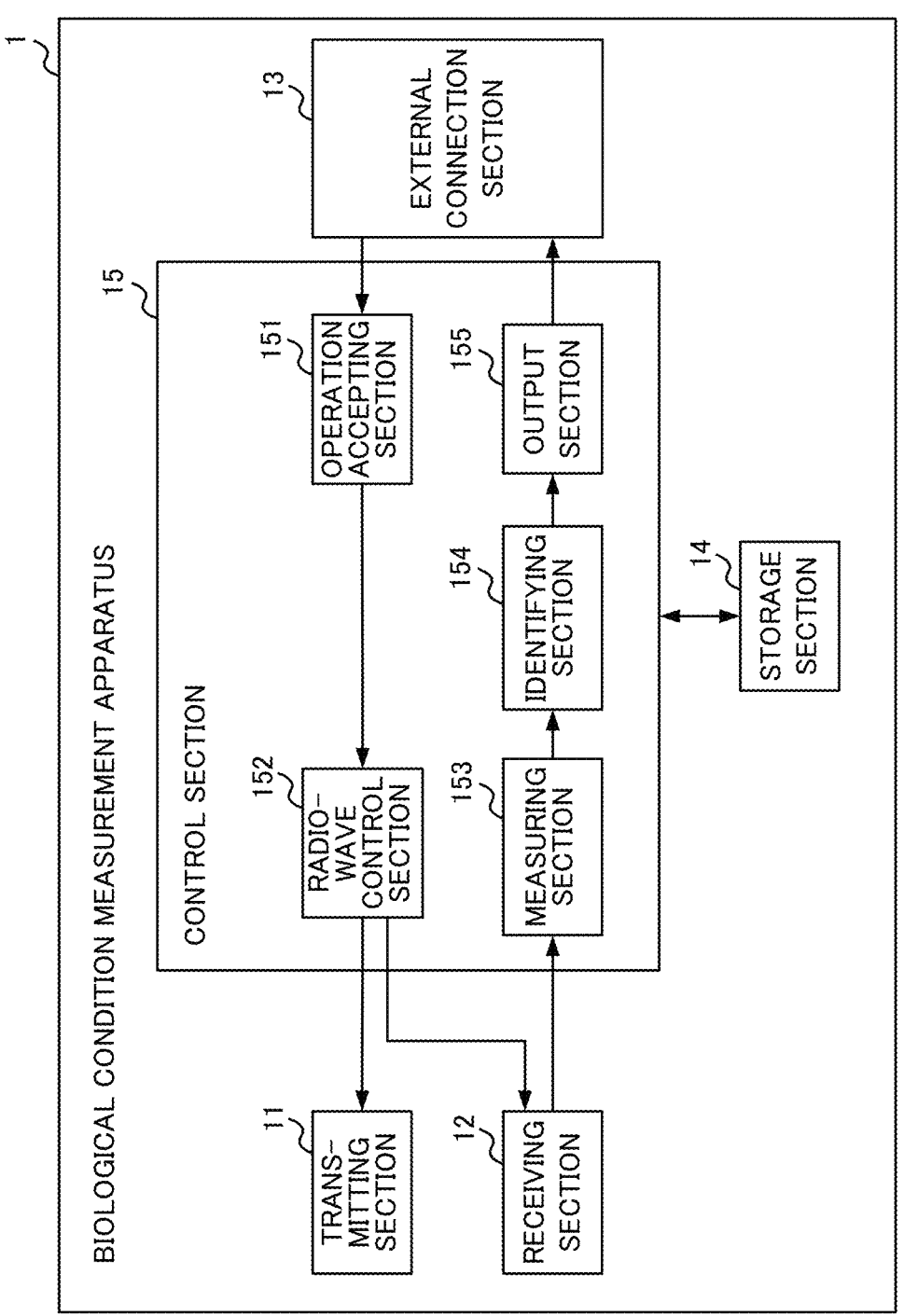
FIG. 4 is a diagram depicting the configuration of a biological condition measurement apparatus 1.

FIG. 4 is a diagram depicting the configuration of the biological condition measurement apparatus 1. The biological condition measurement apparatus 1 has a transmitting section 11, a receiving section 12, an external connection section 13, a storage section 14 and a control section 15. The control section 15 has a operation accepting section 151, a radio-wave control section 152, a measuring section 153, an identifying section 154 and an output section 155.

The transmitting section 11 transmits transmission signals in a frequency band equal to or higher than the millimeter wave band at predetermined time intervals under control of the radio-wave control section 152. For example, the transmitting section 11 transmits chirp signals in cycles of 12.5 milliseconds. The transmitting section 11 has a signal generating circuit that generates chirp signals, and an antenna for transmitting the transmission signals as radio waves. For example, the biological condition measurement apparatus 1 may have a plurality of the transmitting sections 11 that transmit transmission signals toward different areas at mutually different timings.

The transmitting section 11 transmits transmission signals at preset time intervals shorter than the half cycle of the minimum value of cycles in which biological conditions change. For example, in a case where it is assumed that the maximum value of heart rates is 150 times/minute, the minimum value of the fluctuation cycle of the heart rates is 0.4 seconds. In view of this, the transmitting section 11 transmits transmission signals at time intervals shorter than 0.2 seconds. The transmission of transmission signals by the transmitting section 11 at such time intervals allows the biological condition measurement apparatus 1 to identify changed conditions of physical parts of measurement subjects U on the basis of reflection signals received by the receiving section 12 at the time intervals.

The length of transmission signals transmitted by the transmitting section 11 can be any length, but it is desirable if the length is sufficiently shorter than time intervals at which the transmission signals are transmitted, and is equal to or shorter than 2 milliseconds, for example. In a case where the biological condition measurement apparatus 1 has a plurality of transmitting sections 11, the length of transmission signals transmitted by the transmitting sections 11 is determined on the basis of the number of the transmitting sections 11. Specifically, the length of the transmission signals is shorter than a length of time which is the quotient of the length of time intervals at which the transmission signals are transmitted, by the number of the transmitting sections 11. By setting the length of the transmission signals in this manner, the plurality of transmitting sections 11 can transmit the transmission signals at different timings.

The receiving section 12 receives a plurality of reflection signals generated by the reflection of transmission signals on a plurality of measurement subjects U. For example, there are a plurality of the receiving sections 12 that receive reflection signals coming from mutually different areas. The receiving sections 12 input the received reflection signals to the measuring section 153.

Figures 5A, 5B:
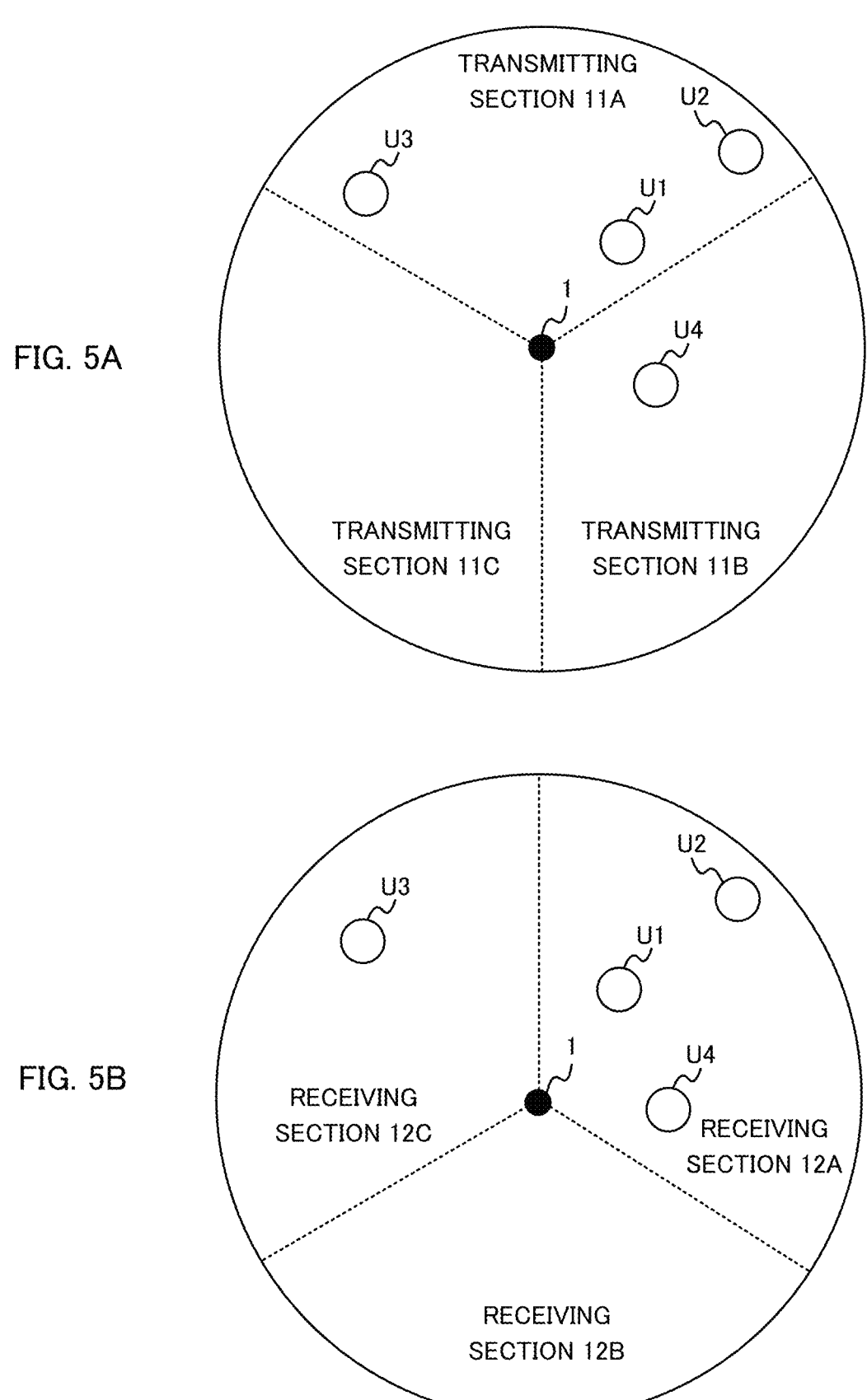
FIGS. 5A and 5B are each a figure for explaining transmission areas of transmitting sections 11 and reception areas of receiving sections 12.

FIGS. 5A and 5B are each a figure for explaining transmission areas of the transmitting sections 11 and reception areas of the receiving sections 12. FIG. 5A schematically depicts an area toward which each of a transmitting section 11A, a transmitting section 11B and a transmitting section 11C transmits transmission signals, and the positions of a plurality of measurement subjects U, in a case where the biological condition measurement apparatus 1 has those transmitting sections 11. FIG. 5B schematically depicts an area from which each of a receiving section 12A, a receiving section 12B and a receiving section 12C receives reflection signals, and the positions of the plurality of measurement subjects U, in a case where the biological condition measurement apparatus 1 has those receiving sections 12.

In the examples depicted in FIGS. 5A and 5B, the transmission area of each transmitting section 11 has a fan shape with ±60 degrees (120 degrees), and the reception area of each receiving section 12 has a fan shape with ±60 degrees (120 degrees). Although not depicted in FIGS. 5A and 5B, the transmitting sections 11 transmit transmission signals in a predetermined vertical range, and the receiving sections 12 receive reflection signals coming from a predetermined vertical range. For example, the predetermined ranges are ranges of ±15 degrees (30 degrees) centered on the horizontal direction.

As depicted in FIGS. 5A and 5B, it is desirable if the transmission areas of the transmitting sections 11 and the reception areas of the receiving section 12 do not match completely. Since the biological condition measurement apparatus 1 can identify that there are measurement subjects U in an area where the transmission area of a transmitting section 11 that transmitted a transmission signal, and the reception area of a receiving section 12 that received reflection signals based on the transmission signal overlap, the number of areas where different pairs of the transmission areas and the reception areas overlap increases in a case where the transmission areas and the reception areas do not match completely, and accordingly the discrimination of the biological condition measurement apparatus 1 to identify the positions of the measurement subjects U increases.

The external connection section 13 has a communication interface for transmitting and receiving data to and from the information terminal 2. For example, the external connection section 13 has a USB interface. The external connection section 13 receives operation data input on the information terminal 2, and inputs the received data to the operation accepting section 151. In addition, the external connection section 13 transmits, to the information terminal 2, data representing measurement results output by the output section 155.

The storage section 14 has a storage medium such as a ROM (Read Only Memory) or a RAM (Random Access Memory). The storage section 14 stores programs to be executed by the control section 15. In addition, the storage section 14 stores reflection signals received by the receiving sections 12, and measurement results generated by analysis of the reflection signals by the control section 15.

For example, the control section 15 has a CPU (Central Processing Unit). The control section 15 functions as the operation accepting section 151, the radio-wave control section 152, the measuring section 153, the identifying section 154 and the output section 155 by executing programs stored on the storage section 14.

The operation accepting section 151 accepts operations by a user by receiving operation data input from the information terminal 2 via the external connection section 13. For example, the operation accepting section 151 accepts an operation to start measurement, an operation to suspend measurement, an operation to end measurement or an operation to update measurement results that is input in the region R2 depicted in FIG. 2.

In addition, the operation accepting section 151 may accept operation to set a target area of identification of biological conditions by the identifying section 154 (hereinafter, called an "identification target area" in some cases). The operation accepting section 151 accepts setting of a range of distance to target measurement subjects U of identification of biological conditions. For example, the operation accepting section 151 may accept setting of a target area of identification of biological conditions to any value in the range from 0 degrees to 360 degrees, relative to a predetermined side (e.g. the front direction) of the biological condition measurement apparatus 1.

For example, the operation accepting section 151 accepts setting of numerical values representing angles like "from 0 degrees to 90 degrees" or "from 270 degrees to 90 degrees." The operation accepting section 151 may accept setting of a target area of identification of biological conditions by causing the information terminal 2 to display a circular image like the one depicted in FIG. 3 via the external connection section 13, and accepting an operation to circle the target area of the identification of biological conditions.

The radio-wave control section 152 controls the transmitting sections 11 and the receiving sections 12. For example, the radio-wave control section 152 controls timings at which the transmitting sections 11 are caused to transmit transmission signals. In addition, the radio-wave control section 152 controls areas toward which the transmitting sections 11 transmit transmission signals and areas from which the receiving sections 12 receive reflection signals.

For example, the radio-wave control section 152 controls the plurality of transmitting sections 11 such that one or more transmitting sections 11 corresponding to identification target areas accepted by the operation accepting section 151 in the plurality of transmitting sections 11 are caused to transmit transmission signals. In addition, the radio-wave control section 152 controls the plurality of receiving sections 12 such that one or more receiving sections 12 corresponding to identification target areas accepted by the operation accepting section 151 in the plurality of receiving sections 12 are caused to receive reflection signals. By the radio-wave control section 152 causing transmitting sections 11 corresponding to identification target areas to transmit transmission signals and causing receiving sections 12 corresponding to identification target areas to receive reflection signals in this manner, it becomes less likely to be influenced by unnecessary reflection signals coming from areas where there are no measurement subjects U, and accordingly the measurement precision improves.

By performing digital signal processing on reflection signals received by receiving sections 12, the measuring section 153 measures a plurality of times of flight from transmission of transmission signals by transmitting sections 11 until reception of a plurality of reflection signals by the receiving sections 12 in order to identify the distances from the biological condition measurement apparatus 1 to measurement subjects U and the directions of the measurement subjects U relative to the biological condition measurement apparatus 1. In a case where the biological condition measurement apparatus 1 has a plurality of receiving sections 12, the measuring section 153 measures, for each receiving section 12, the time of flight from transmission of a transmission signal by a transmitting section 11 until reception of reflection signals by the plurality of receiving sections 12.

The measuring section 153 may measure, as a time of flight, the frequency of a chirp signal included in a transmission signal or the phase of a transmission signal. Since the frequency of a chirp signal or the phase of a transmission signal is equivalent to a time of flight, measurement of the frequency of the chirp signal or the phase of the transmission signal by the measuring section 153 also can be regarded as measurement of the time of flight.

In a case where the biological condition measurement apparatus 1 has a plurality of transmitting sections 11, the measuring section 153 measures, for each transmitting section 11, the time of flight from transmission of a transmission signal by each of the plurality of transmitting sections 11 until reception of reflection signals by receiving sections 12. The measuring section 153 stores, on the storage section 14, time-of-flight data representing the measured times of flight in association with the respective transmitting sections 11. In a case where the biological condition measurement apparatus 1 has a plurality of receiving sections 12, the measuring section 153 measures, for each receiving section 12, the time of flight from transmission of a transmission signal by a transmitting section 11 until reception of reflection signals by the plurality of receiving sections 12. The measuring section 153 stores, on the storage section 14, time-of-flight data representing the measured times of flight in association with the respective receiving sections 12.

In a case where the biological condition measurement apparatus 1 has a plurality of transmitting sections 11 and a plurality of receiving sections 12, the measuring section 153 measures, for each combination of a transmitting section 11 and a receiving section 12, the time of flight from transmission of a transmission signal from each of the plurality of transmitting sections 11 until reception of reflection signals by the plurality of receiving sections 12. The measuring section 153 stores, on the storage section 14, time-of-flight data representing the measured times of flight in association with the combinations of the transmitting sections 11 and the receiving sections 12.

By analyzing a reflection signal, the measuring section 153 identifies three elements which are the distance between the biological condition measurement apparatus 1 and a measurement subject U, and the direction of the measurement subject U and the movement speed of the measurement subject U relative to the biological condition measurement apparatus 1. The measuring section 153 identifies the distance between the biological condition measurement apparatus 1 and the measurement subject U on the basis of times of flight. The measuring section 153 identifies the direction of the measurement subject U on the basis of a combination of a transmitting section 11 that transmitted a transmission signal and a receiving section 12 that received a reflection signal. The measuring section 153 identifies the movement speed of the measurement subject U on the basis of change amounts of times of flight and change amounts of the direction of the measurement subject U. The measuring section 153 may identify the movement speed of the measurement subject U by calculating angular frequencies on the basis of the magnitudes of changes of the phases of reflection signals based on chirp signals transmitted at certain time intervals.

Although any method can be used by the measuring section 153 to identify times of flight on the basis of reflection signals, in order to reduce the influence of noise, the measuring section 153 transforms the reflection signals into frequency-domain signals by the Fourier transform on the reflection signals, for example. The measuring section 153 identifies a frequency component included in a chirp signal included in a reflection signal in the frequency domain, and identifies, as a time of flight, the difference between a time at which a transmitting section 11 transmitted the frequency component and a time at which a receiving section 12 received the frequency component included in the reflection signal. In order to improve the measurement precision, the measuring section 153 may measure a time of flight by identifying the times of flight of a plurality of frequency components included in a transmission signal, and calculating a statistic (e.g. the average or the median) of a plurality of the identified times of flight.

Figure 6:
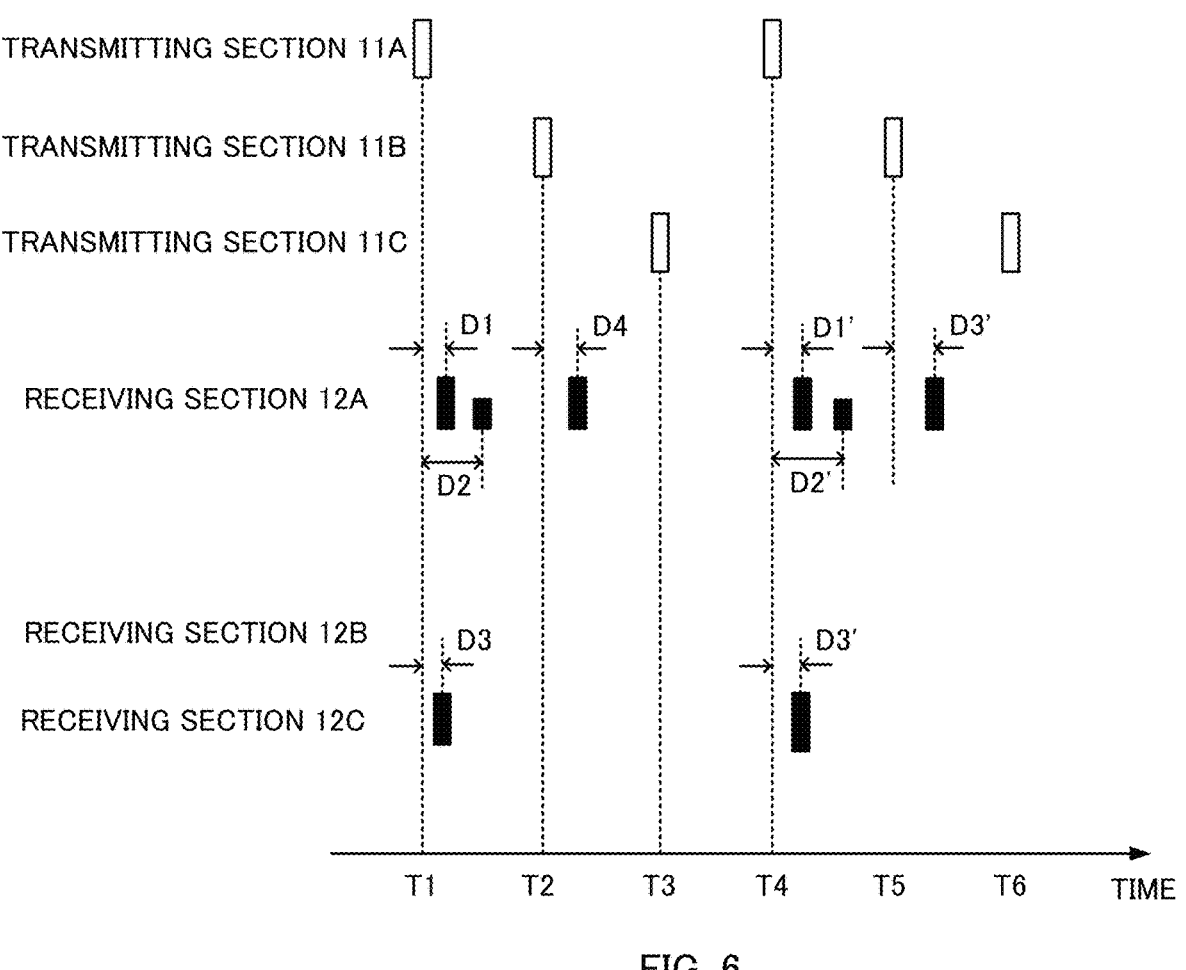
FIG. 6 is a figure for explaining an operation of a measuring section 153.

FIG. 6 is a figure for explaining an operation of the measuring section 153. White oblongs in FIG. 6 represent transmission signals transmitted by the transmitting sections 11, and black oblongs in FIG. 6 represent reflection signals received by the receiving sections 12. In the example depicted in FIG. 6, the transmitting section 11A, the transmitting section 11B and the transmitting section 11C sequentially transmit transmission signals at times T1, T2 and T3, and subsequently the transmitting section 11A, the transmitting section 11B and the transmitting section 11C sequentially transmit transmission signals at times T4, T5 and T6.

As depicted in FIG. 6, cycles in which the transmitting sections 11 transmit transmission signals are set to have a length of time that is longer than ((time length of transmission signals)+(length of time during which reflection signals may be received))×(number of transmitting sections 11). By determining the cycles in which transmission signals are transmitted in this manner, it is possible to prevent simultaneous arrivals of reflection signals of transmission signals transmitted by the plurality of transmitting sections 11 at the biological condition measurement apparatus 1.

The measuring section 153 measures a length of time that elapses from the transmission of a transmission signal by each of the transmitting section 11A, the transmitting section 11B and the transmitting section 11C until reception of a reflection signal. In the case of the example depicted in FIG. 6, the measuring section 153 measures reception of a reflection signal by the receiving section 12A after a lapse of a length of time D1 after the transmission of the transmission signal by the transmitting section 11A at the time T1. The reflection signal is a reflection signal generated by reflection of the transmission signal transmitted by the transmitting section 11A on the measurement subject U1 in the examples depicted in FIGS. 5A and 5B.

In addition, the measuring section 153 measures reception of a reflection signal by the receiving section 12A also after a lapse of a length of time D2 after the transmission of the transmission signal by the transmitting section 11A. The reflection signal is a reflection signal generated by reflection of the transmission signal transmitted by the transmitting section 11A on a measurement subject U2 in the examples depicted in FIGS. 5A and 5B. Furthermore, the measuring section 153 measures reception of a reflection signal by the receiving section 12C also after a lapse of a length of time D3 after the transmission of the transmission signal by the transmitting section 11A. The reflection signal is a reflection signal generated by reflection of the transmission signal transmitted by the transmitting section 11A on a measurement subject U3 in the examples depicted in FIGS. 5A and 5B.

Similarly, the measuring section 153 measures reception of a reflection signal by the receiving section 12A after a lapse of a length of time D4 after the transmission of the transmission signal by the transmitting section 11B. The reflection signal is a reflection signal generated by reflection of the transmission signal transmitted by the transmitting section 11B on a measurement subject U4 in the examples depicted in FIGS. 5A and 5B.

The measuring section 153 repeats similar processes also after the time T4. As depicted in FIG. 6, the times of flight D1 to D4 from the transmission of the transmission signals by the transmitting sections 11 until the reception of the reflection signals by the receiving sections 12 changed to different D1' to D4'. This is caused by changes of the distances between parts that reflected the transmission signals on the measurement subject U1 to the measurement subject U4 and the biological condition measurement apparatus 1 due to motions of the parts.

The measuring section 153 may further measure the levels of reflection signals received by receiving sections 12, and store, on the storage section 14, the measured levels of the reflection signals along with the times of flight. Since attenuation amounts of the signals vary depending on the distances between the biological condition measurement apparatus 1 and measurement subjects U, as depicted in FIG. 6, it is considered that the levels of reflection signals lower as the times of flight increase. In a case where the level of a reflection signal with a long time of flight is higher than the level of a reflection signal with a short time of flight, the measuring section 153 may determine that the reflection signals may include noise, and not store the times of flight of the reflection signals on the storage section 14.

The identifying section 154 identifies biological conditions of each of a plurality of measurement subjects U on the basis of times of flight measured by the measuring section 153. In a case where the biological condition measurement apparatus 1 has a plurality of transmitting sections 11, the identifying section 154 identifies biological conditions of a plurality of measurement subjects U in areas toward which the plurality of transmitting sections 11 transmit transmission signals. In a case where the biological condition measurement apparatus 1 has a plurality of receiving sections 12, the identifying section 154 identifies biological conditions of a plurality of measurement subjects in areas from which the plurality of receiving sections 12 receive reflection signals.

In a case where the biological condition measurement apparatus 1 has a plurality of transmitting sections 11 and a plurality of receiving sections 12, the identifying section 154 identifies biological conditions of a plurality of measurement subjects in each of a plurality of areas that are determined from combinations of areas toward which the plurality of transmitting sections 11 transmit transmission signals and areas from which the plurality of receiving sections 12 receive reflection signals, on the basis of times of flight measured by the measuring section 153 for each combination of a transmitting section 11 and a receiving section 12. By being configured in this manner, the biological condition measurement apparatus 1 can identify biological conditions of each measurement subject U even in a case where there are a plurality of measurement subjects U at the same distance from the biological condition measurement apparatus 1.

In order to identify biological conditions of a plurality of measurement subjects U, the identifying section 154 creates waveforms representing cardiac motions, waveforms representing pleural motions or the like first by identifying changes of the distance between the biological condition measurement apparatus 1 and a part that reflected transmission signals on each of the plurality of measurement subjects U, on the basis of changes of times of flight measured by the measuring section 153. By identifying the cycles of the waveforms, the identifying section 154 identifies biological conditions such as a heart rate or a respiratory rate per unit time.

As depicted in FIG. 6, in a case where transmission signals were reflected on a plurality of measurement subjects U, a receiving section 12 receives a plurality of reflection signals based on one transmission signal. The identifying section 154 performs a process in the following manner in order to identify a time of flight corresponding to each of a plurality of measurement subjects U.

First, the identifying section 154 classifies time-of-flight data representing a plurality of times of flight measured by the measuring section 153 into a plurality of pieces of time series data including a plurality of pieces of time-of-flight data representing times of flight that fluctuate within a time range equal to or lower than a first threshold, and identifies biological conditions of each of the plurality of measurement subjects U on the basis of changes in each time interval of times of flight represented by each of the plurality of pieces of time series data. The first threshold is a value that is higher than the maximum value of change amounts of times of flight caused by motions of an organ of one measurement subject U, and additionally is smaller than an expected minimum value of differences from times of flight of reflection signals from other measurement subjects U. The identifying section 154 stores, on the storage section 14, the identified biological conditions in association with the measurement subjects U.

The maximum value of change amounts of times of flight caused by motions of an organ of a measurement subject U corresponds to an expected greatest amount (e.g. 5 cm) of amounts of displacement of the position of the organ in a stationary state of the measurement subject U, and the differences from the times of flight of the reflection signals from the other measurement subjects U correspond to a distance difference of 50 cm, for example. That is, the first threshold is a length of time required for radio waves to be propagated over any distance that is equal to or longer than 5 cm and is shorter than 50 cm.

FIG. 6 depicts a case where the difference between the times of flight of the reflection signal whose delay from the time T1 is D1 and the reflection signal whose delay from the time T4 which is a predetermined time interval after the time T1 is D1' is shorter than the first threshold. The measuring section 153 determines that these reflection signals are reflection signals corresponding to the same measurement subject U. In addition, FIG. 6 depicts a case where the difference between the times of flight of the reflection signal whose delay from the time T1 is D1 and the reflection signal whose delay from the time T4 is D2' is equal to or higher than the first threshold. The measuring section 153 determines that these reflection signals are reflection signals corresponding to mutually different measurement subjects U.

Figure 7:
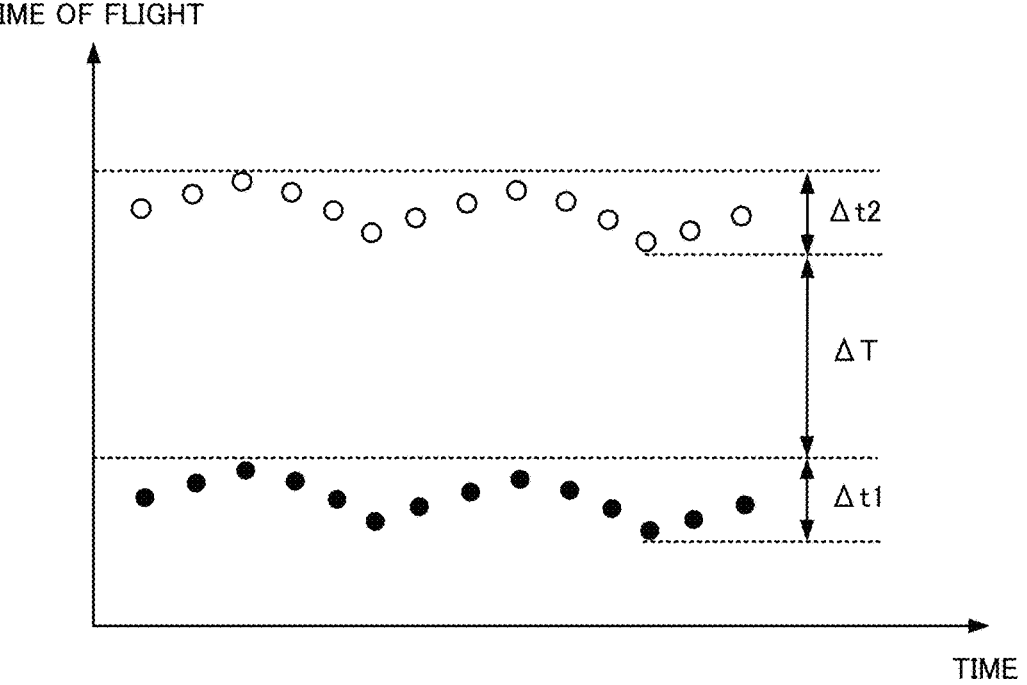
FIG. 7 is a figure for explaining an operation of an identifying section 154.

FIG. 7 is a figure for explaining an operation of the identifying section 154. The horizontal axis in FIG. 7 represents times, and the vertical axis in FIG. 7 represents times of flight measured by the measuring section 153 at each time. Black circles in FIG. 7 represent the times of flight of reflection signals corresponding to the measurement subject U1, and white circles in FIG. 7 represent the times of flight of reflection signals corresponding to the measurement subject U2. The extent of fluctuation of a plurality of the times of flight represented by the black circles in one cycle is Δt1, the extent of fluctuation of a plurality of the times of flight represented by the white circles in one cycle is Δt2, and these are shorter than the first threshold. On the other hand, the minimum value ΔT of differences between the times of flight represented by the black circles and the times of flight represented by the white circles is equal to or higher than the first threshold.

In this case, the identifying section 154 classifies the plurality of pieces of time-of-flight data into first time series data corresponding to the plurality of times of flight represented by the black circles and second time series data corresponding to the plurality of times of flight represented by the white circles. Then, the identifying section 154 identifies biological conditions of the measurement subject U1 on the basis of the first time series data, and identifies biological conditions of the measurement subject U2 on the basis of the second time series data. By operating in this manner, the identifying section 154 can identify biological conditions of each of a plurality of measurement subjects U even in a case where receiving sections 12 received a plurality of reflection signals based on a transmission signal transmitted by one transmitting section 11.

After identifying the biological conditions of the plurality of measurement subjects U, the identifying section 154 may track the biological conditions of the measurement subjects U who are moving, on the basis of times of flight. The identifying section 154 identifies, as biological conditions of one measurement subject U, time series data including a plurality of pieces of time-of-flight data representing times of flight that fluctuate in a time range equal to or lower than a second threshold higher than the first threshold in cycles during which the times of flight fluctuate, and stores, on the storage section 14, the identified biological conditions in association with the measurement subject U. The second threshold is a value that is higher than the maximum value of change amounts of times of flight in a predetermined length of time (e.g. in one cycle during which times of flight fluctuate) caused by a movement of one measurement subject U, and additionally is smaller than the differences from times of flight of reflection signals from other measurement subjects U.

Figure 8:
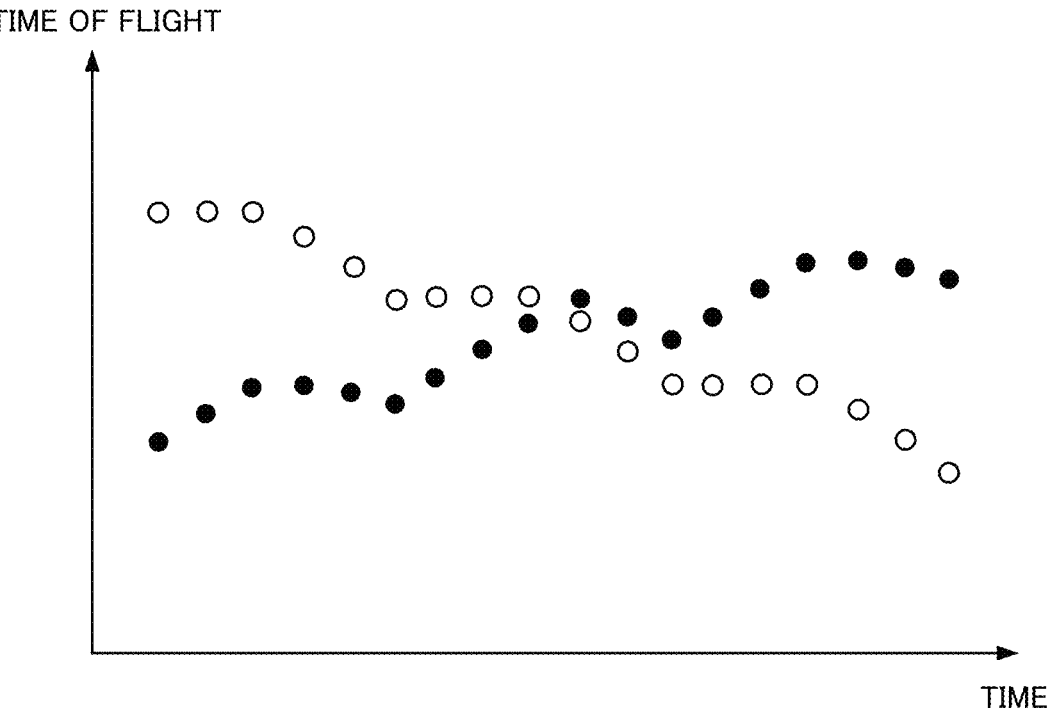
FIG. 8 is a figure for explaining a process in which the identifying section 154 tracks biological conditions of measurement subjects U.

FIG. 8 is a figure for explaining a process in which the identifying section 154 tracks biological conditions of measurement subjects U. Similarly to FIG. 7, black circles in FIG. 8 represent the times of flight of reflection signals corresponding to the measurement subject U1, and white circles in FIG. 8 represent the times of flight of reflection signals corresponding to the measurement subject U2.

FIG. 8 depicts a case where the measurement subject U1 and the measurement subject U2 are moving, and the times of flight change with time. Specifically, the measurement subject U1 is moving away from the biological condition measurement apparatus 1 with time, and the measurement subject U2 is moving toward the biological condition measurement apparatus 1 with time. The identifying section 154 identifies first time series data corresponding to the measurement subject U1 represented by black, and second time series data corresponding to the measurement subject U2 represented by white by selecting a plurality of pieces of time-of-flight data representing times of flight whose fluctuation ranges are equal to or shorter than the second threshold for each fluctuation cycle of time of flights in a plurality of pieces of time-of-flight data.

At a time when the positions of the measurement subject U1 and the measurement subject U2 become almost the same, the identifying section 154 may identify time-of-flight data corresponding to each of the measurement subjects U on the basis of features of waveforms (e.g. amplitudes or cycles) formed by linking the preceding and following pieces of time-of-flight data. Specifically, in case where it is unknown to which measurement subject U time-of-flight data corresponds, the identifying section 154 assumes that the time-of-flight data is time-of-flight data of either measurement subject U, and identifies features of a waveform of a cycle including the time-of-flight data. In a case where the identified features match features of the past cycles, the identifying section 154 determines that the assumption is correct, and in a case where the identified features do not match features of the past cycles, the identifying section 154 determines that the assumption is wrong, and identifies that the time-of-flight data corresponds to another measurement subject U.

The identifying section 154 may identify biological conditions corresponding to each of a plurality of parts of a measurement subject U. For example, the identifying section 154 identifies the parts on the basis of the times of flight of a plurality of reflection signals generated by the reflection of transmission signals on a plurality of parts like cardiac motions, carotid artery motions, pleural motions, head motions or the like of the measurement subject U. By classifying a plurality of the reflection signals generated by the reflection of one transmission signal transmitted by a transmitting section 11 on the plurality of parts of the measurement subject U on the basis of a range in which times of flight measured by the measuring section 153 are included, the identifying section 154 identifies a plurality of biological conditions corresponding to the plurality of parts. By the identifying section 154 operating in this manner, a plurality of biological conditions of a measurement subject U can be identified.

The identifying section 154 may identify the positions of a plurality of measurement subjects U. Specifically, the identifying section 154 identifies the positions of measurement subjects U that generated reflection signals on the basis of: areas from which receiving sections 12 that received the reflection signals receive the reflection signals; areas toward which transmitting sections 11 that transmitted transmission signals to generate the reflection signals transmit the transmission signals; and the distances to the measurement subjects U corresponding to times of flight.

In the example depicted in FIG. 5A, a transmission signal transmitted by the transmitting section 11A is reflected on the measurement subject U1, the measurement subject U2 and the measurement subject U3, and a transmission signal transmitted by the transmitting section 11B is reflected on the measurement subject U4. Then, reflection signals generated by the reflection on the measurement subject U1, the measurement subject U2 and the measurement subject U4 are received by the receiving section 12A, and a reflection signal generated by the reflection on the measurement subject U3 is received by the receiving section 12C.

In a case where reflection signals based on the transmission signal transmitted by the transmitting section 11A are received by the receiving section 12A, the identifying section 154 identifies that the measurement subject U1 and the measurement subject U2 that reflected the transmission signal are in a region where the transmission area of the transmitting section 11A and the reception area of the receiving section 12A overlap. In addition, in a case where a reflection signal based on the transmission signal transmitted by the transmitting section 11A is received by the receiving section 12C, the identifying section 154 identifies that the measurement subject U3 that reflected the transmission signal is in a region where the transmission area of the transmitting section 11A and the reception area of the receiving section 12C overlap.

The identifying section 154 further identifies the distances between the biological condition measurement apparatus 1 and measurement subjects U on the basis of times of flight. The identifying section 154 can identify the positions of a plurality of measurement subjects U relative to the biological condition measurement apparatus 1 on the basis of regions where the measurement subjects U are and the distances from the biological condition measurement apparatus 1 to the measurement subjects U.

The output section 155 outputs, in association with each other, biological conditions and information representing the positions of measurement subjects U identified by the identifying section 154. Specifically, the output section 155 causes the information terminal 2 to display the screen representing the biological conditions depicted in FIG. 2 and the screen representing the positions of the measurement subjects U depicted in FIG. 3, outputs these pieces of data to a printer, transmits these pieces of data to an external apparatus via a communication line, and so on.

For example, as depicted in FIG. 2, the output section 155 prioritizes output of biological conditions corresponding to a measurement subject U identified as being the closest to the biological condition measurement apparatus 1 on the basis of times of flight in a plurality of biological conditions corresponding to a plurality of measurement subjects U identified by the identifying section 154, over output of biological conditions corresponding to other measurement subjects U. For example, the output section 155 causes the information terminal 2 to display biological conditions sequentially starting from a measurement subject U closer to the biological condition measurement apparatus 1, causes the information terminal 2 to display only biological conditions of a measurement subject U closest to the biological condition measurement apparatus 1, and so on. By the output section 155 operating in this manner, in a case where there are many humans in a room where the biological condition measurement apparatus 1 is used, it becomes easier for a user to grasp biological conditions of measurement subjects U whose biological conditions are desired to be measured.

[Processing Procedure in Biological Condition Measurement Apparatus 1]

Figure 9:
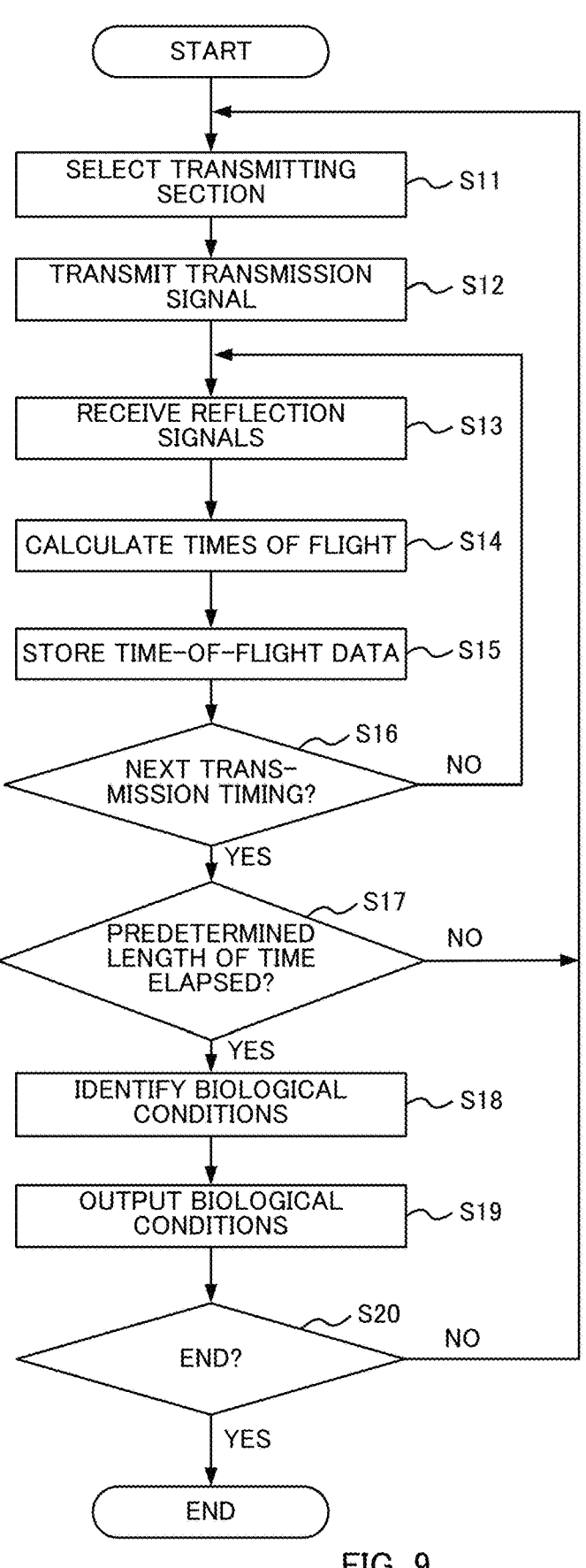
FIG. 9 is a flowchart depicting a processing procedure in the biological condition measurement apparatus 1.

FIG. 9 is a flowchart depicting a processing procedure in the biological condition measurement apparatus 1. The flowchart depicted in FIG. 9 starts at a time point when a user of the biological condition measurement apparatus 1 performed operation to start measurement.

The radio-wave control section 152 selects a transmitting section 11 to be caused to transmit a transmission signal from a plurality of transmitting sections 11 on the basis of a time (S11). In the case of the example depicted in FIG. 6, the radio-wave control section 152 selects the transmitting section 11A at the time T1. The radio-wave control section 152 causes the selected transmitting section 11 to transmit a transmission signal (S12).

Next, a receiving section 12 receives reflection signals based on the transmission signal (S13). The measuring section 153 calculates a time of flight required for the reflection signals to be received by the receiving section 12 after the transmission of the transmission signal (S14). The measuring section 153 stores, on the storage section 14, time-of-flight data in association with the combination of the transmitting section 11 that transmitted the transmission signal and the receiving section 12 that received the reflection signals (S15).

The radio-wave control section 152 determines whether or not the next transmission timing (e.g. a time T2) has come (S16). In a case where the radio-wave control section 152 determined that the next transmission timing has not come (NO at S16), the radio-wave control section 152 does not cause any transmitting section 11 to transmit a transmission signal, and the processes from S13 to S16 are repeated.

In a case where the radio-wave control section 152 determined that the next transmission timing has come (YES at S16), the identifying section 154 determines whether or not a predetermined length of time has elapsed after the start of transmission of transmission signals by transmitting sections 11, and a timing to identify biological conditions has come (S17). The predetermined length of time is a length of time required for storing a number pieces of time-of-flight data necessary for the identifying section 154 to identify biological conditions. The predetermined length of time is a length of time longer than one cycle of biological conditions, and is equal to or longer than 30 seconds, for example.

In a case where the identifying section 154 determined that the predetermined length of time has not elapsed (NO at S17), the radio-wave control section 152 selects the next transmitting section 11 (S11), and the processes from S11 to S17 are repeated. In a case where the identifying section 154 determined that the predetermined length of time has elapsed (YES at S17), the identifying section 154 identifies biological conditions on the basis of the time-of-flight data stored on the storage section 14 (S18). The output section 155 outputs the biological conditions identified by the identifying section 154 (S19). The biological condition measurement apparatus 1 repeats the processes from S11 to S20 until the operation accepting section 151 accepts operation to end the processes (YES at S20).

Modification Example

Whereas the biological condition measurement apparatus 1 identifies biological conditions of a plurality of measurement subjects U in the case illustrated in the explanation above, some of the functions of the control section 15 of the biological condition measurement apparatus 1 in the explanation described above may be realized by a second information processing apparatus (e.g. a computer in a cloud). That is, the biological condition measurement apparatus 1 and the second information processing apparatus may operate in a coordinated manner to thereby function as a biological condition measurement system.

For example, the biological condition measurement apparatus 1 sequentially transmits received reflection signals to an external computer. In this case, the external computer executes at least some of the functions of the measuring section 153, the identifying section 154 and the output section 155. Specifically, the external computer classifies reflection signals of each of a plurality of measurement subjects U, identifies biological conditions on the basis of times of flight, and transmits results of the identification to the biological condition measurement apparatus 1. The external computer may transmit the results of the identification to the information terminal 2.

In such a biological condition measurement system, the external computer may receive reflection signals from a plurality of the biological condition measurement apparatuses 1, and identify biological conditions of a plurality of measurement subjects U corresponding to the reflection signals received by the plurality of biological condition measurement apparatuses 1. Such configuration is suitable for a case where there are many measurement subjects U in a plurality of rooms.

[Effects Attained with Biological Condition Measurement Apparatus 1]

As explained above, the measuring section 153 measures a plurality of times of flight from transmission of transmission signals by transmitting sections 11 until reception of a plurality of reflection signals by receiving sections 12. Then, the identifying section 154 classifies a plurality of pieces of time-of-flight data representing a plurality of times of flight into a plurality of pieces of time series data including a plurality of pieces of time-of-flight data representing times of flight that fluctuate within a time range equal to or lower than the first threshold, and identifies biological conditions of each of a plurality of measurement subjects U on the basis of modes of change of times of flight represented by each of the plurality of pieces of time series data. By being configured in this manner, the biological condition measurement apparatus 1 can measure biological conditions such as heart rates or respiratory rates even in a case where there are a plurality of humans in an area toward which radio waves are transmitted.

In addition, the biological condition measurement apparatus 1 has a plurality of transmitting sections 11 that transmit transmission signals toward different areas at mutually different timings, and a plurality of receiving sections 12 that receive reflection signals coming from mutually different areas. Then, the identifying section 154 identifies biological conditions of a plurality of measurement subjects U in each of a plurality of areas that are determined from combinations of areas toward which the plurality of transmitting sections 11 transmit transmission signals and areas from which the plurality of receiving sections 12 receive reflection signals, on the basis of times of flight measured by the measuring section 153 for each combination of a transmitting section 11 and a receiving section 12. By being configured in this manner, the biological condition measurement apparatus 1 can identify biological conditions of each measurement subject U even in a case where there are a plurality of measurement subjects U at the same distance from the biological condition measurement apparatus 1.

Although the present invention has been explained thus far by using an embodiment, the technical scope of the present invention is not limited by the scope of the description of the embodiment described above, but can be modified and varied variously within the scope of the gist. For example, all or some of apparatuses can be configured in a functionally or physically distributed/integrated manner in any units. In addition, embodiments of the present invention include also new embodiments that are generated by combining any ones of a plurality of embodiments. Effects of the new embodiments generated by the combination combine effects of the original embodiments.

What is claimed is:

1. A biological condition measurement apparatus comprising:

one or more transmitting sections each configured to transmit a transmission signal in a frequency band equal to or higher than a millimeter wave band at predetermined time intervals;

one or more receiving sections each configured to receive a plurality of reflection signals generated by reflection of the transmission signal on a plurality of persons;

a measuring section that measures a plurality of times of flight from the transmission of the transmission signal by the one or more transmitting sections until the reception of the plurality of reflection signals by the one or more receiving sections; and an identifying section that classifies a plurality of pieces of time-of-flight data representing the plurality of times of flight into a plurality of pieces of time series data including a plurality of pieces of time-of-flight data representing times of flight that fluctuate in a time range equal to or lower than a first threshold, and identifies a biological condition representing motions of an organ of a first person of the plurality of persons on a basis of a mode of change of times of flight represented by each of the plurality of pieces of time series data, wherein the first threshold is a value that is higher than a maximum value of change amounts of times of flight caused by motions of the organ of the first person, and additionally is smaller than a minimum difference between a time of flight of a reflection signal from the first person and a time of flight of a reflection signal from a second person of the plurality of persons.

2. The biological condition measurement apparatus according to claim 1, wherein, in a case where the one or more receiving sections receive a plurality of the reflection signals based on the transmission signal transmitted by the one or more transmitting sections, the identifying section identifies, as the biological condition of the first person, time series data including a plurality of pieces of time-of-flight data representing times of flight that fluctuate in a time range equal to or lower than a second threshold higher than the first threshold and set to detect movement of the first person larger than organ motions, during a cycle in which the times of flight fluctuate.

3. The biological condition measurement apparatus according to claim 2, wherein the second threshold is a value that is higher than a maximum value of change amounts of times of flight caused by a movement of the first person, and smaller than a minimum difference between a time of flight of a reflection signal from the first person and a time of flight of a reflection signal from the second person.

4. The biological condition measurement apparatus according to claim 1, wherein, by classifying a plurality of the reflection signals generated by reflection of one transmission signal transmitted by the one or more transmitting sections on a plurality of parts of the persons on a basis of a range in which the times of flight measured by the one or more measuring sections are included, the identifying section identifies a plurality of the biological conditions corresponding to the plurality of parts.

5. The biological condition measurement apparatus according to claim 1, wherein the one or more transmitting sections are each configured to transmit the transmission signal at preset time intervals that are shorter than a half cycle of a minimum value of a cycle during which the biological condition changes.

6. The biological condition measurement apparatus according to claim 5, each of the transmission signals is transmitted toward mutually different areas, and has a length shorter than a length of time which is a quotient of a length of the time intervals by a number of the transmitting sections.

7. The biological condition measurement apparatus according to claim 1, wherein the one or more transmitting sections are each configured to transmit the transmission signal in a cycle longer than a value which is obtained by multiplying a sum of a time length of the transmission signal and a length of time during which the reflection signal may be received, by a number of the one or more transmitting sections.

8. The biological condition measurement apparatus according to claim 1, wherein the one or more transmitting sections are configured to transmit the transmission signal toward different areas at mutually different timings, the one or more measuring sections measure, for each of the one or more transmitting sections, at least one of the plurality of time of flights from the transmission of the transmission signal by each of the one or more transmitting sections until the reception of the reflection signal by the one or more receiving sections, and the identifying section identifies the biological condition of the plurality of the persons present in the different areas.

9. The biological condition measurement apparatus according to claim 1, wherein the one or more receiving sections are configured to receive the plurality of reflection signals coming from mutually different areas, the measuring section measures, for each of the one or more receiving sections, a time of flight from the transmission of the transmission signal by each of the one or more transmitting sections until the reception of the reflection signals by the one or more receiving sections, and the identifying section identifies the biological condition of the plurality of the persons present in the mutually different areas from which the one or more receiving sections receive the reflection signals.

10. The biological condition measurement apparatus according to claim 1, wherein the one or more transmitting sections transmit the transmission signal toward different areas at mutually different timings, and the one or more receiving sections receive the reflection signals coming from mutually different areas, the measuring section measures, for each combination of the one or more transmitting sections and the one or more receiving sections, at least one of the plurality of times of flight from the transmission of the transmission signals by each of the one or more transmitting sections until the reception of the reflection signals by the one or more receiving sections, and the identifying section identifies the biological condition of the plurality of the persons in areas determined from combinations of the areas toward which the one or more transmitting sections transmit the transmission signal and the areas from which the one or more receiving sections receive the reflection signals, on a basis of the at least one time of flight measured by the measuring section for each combination of the one or more transmitting sections and the one or more receiving sections.

11. The biological condition measurement apparatus according to claim 10, further comprising:

an operation accepting section that accepts operation to set a target area of the identification of the biological condition by the identifying section; and a radio-wave control section that controls the one or more transmitting sections and the one or more receiving sections such that the one or more transmitting sections corresponding to the target area accepted by the operation accepting section in the one or more transmitting sections are caused to transmit the transmission signal, and the one or more receiving sections corresponding to the target area accepted by the operation accepting section in the one or more receiving sections are caused to receive the reflection signals.

12. The biological condition measurement apparatus according to claim 1, wherein the identifying section identifies a position of the first person that generates the reflection signals, on a basis of: an area from which the one or more receiving sections receives the reflection signals; an area toward which the one or more transmitting sections transmits the transmission signal to generate the reflection signals; and a distance to the first person corresponding to at least one of the plurality of times of flight, and the biological condition measurement apparatus further comprises an output section that outputs, in association with each other, the biological condition and information representing the position of the first person identified by the identifying section.

13. The biological condition measurement apparatus according to claim 12, wherein the area from which the receiving section receives the reflection signal and the area toward which the transmitting section transmits the transmission signal are different, and additionally partially overlap.

14. The biological condition measurement apparatus according to claim 1, further comprising an output section that prioritizes output of the biological condition corresponding to the first person identified as being the closest to the biological condition measurement apparatus on a basis of the plurality of time of flights in a plurality of the biological conditions corresponding to the plurality of the persons identified by the identifying section, over output of the biological condition corresponding to the second person.

15. The biological condition measurement apparatus according to claim 1, wherein in a case where it is unknown to which person's time-of-flight data corresponds, and a feature identified by assuming that the time-of-flight data is first time-of flight data of the person matches a feature of a past cycle of the one of the plurality of the persons, the identifying section determines that the assumption is correct, and in a case that the feature does not match the feature of the past cycle of the one of the plurality of the persons, the identifying section determines that the assumption is wrong, and determines that the first time-of-flight data corresponds to another person in the plurality of the persons.

16. A biological condition measurement apparatus, comprising:

one or more transmitting sections each configured to transmit a transmission signal in a frequency band equal to or higher than a millimeter wave band at predetermined time intervals;

one or more receiving sections each configured to receive a plurality of reflection signals generated by reflection of the transmission signal on a plurality of persons;

a measuring section that measures a plurality of times of flight from the transmission of the transmission signal by the one or more transmitting sections until the reception of the plurality of reflection signals by the one or more receiving sections; and an identifying section that classifies a plurality of pieces of time-of-flight data representing the plurality of times of flight into a plurality of pieces of time series data including a plurality of pieces of time-of-flight data representing times of flight that fluctuate in a time range equal to or lower than a first threshold, and identifies a biological condition representing motions of an organ of each of the plurality of the persons on a basis of a mode of change of times of flight represented by each of the plurality of pieces of time series data, wherein the measuring section measures levels of a plurality of reflection signals received by the one or more receiving sections, in a case where a level of a reflection signal of the plurality of reflection signals with a long time of flight is equal to or lower than a level of a reflection signal of the plurality of reflection signals with a short time of flight, the measuring section causes the times of flight of the plurality of reflection signals to be stored on a storage section, and in a case where a level of the reflection signal with the long time of flight is higher than the level of the reflection signal with the short time of flight, the measuring section does not cause the times of flight of the plurality of reflection signals to be stored on the storage section.

17. A biological condition measurement method executed by a computer comprising:

a step of transmitting a transmission signal in a frequency band equal to or higher than a millimeter wave band at predetermined time intervals;

a step of receiving a plurality of reflection signals generated by reflection of the transmission signal on a plurality of persons;

a step of measuring a plurality of times of flight from the transmission of the transmission signal until the reception of the plurality of reflection signals; and a step of classifying a plurality of pieces of time-of-flight data representing the plurality of times of flight into a plurality of pieces of time series data including a plurality of pieces of time-of-flight data representing times of flight that fluctuate in a time range equal to or lower than a first threshold, and identifying a biological condition representing motions of an organ of a first person of the plurality of the persons on a basis of a mode of change of times of flight represented by each of the plurality of pieces of time series data, wherein the first threshold is a value that is higher than a maximum value of change amounts of times of flight caused by motions of the organ of the first person, and additionally is smaller than a minimum difference between a time of flight of a reflection signal from the first person and a time of flight of a reflection signal from a second person of the plurality of persons.

18. A biological condition measurement system comprising: a biological condition measurement apparatus; and an information processing apparatus that can communicate with the biological condition measurement apparatus, wherein the biological condition measurement apparatus comprises:

one or more transmitting sections each configured to transmit a transmission signal in a frequency band equal to or higher than a millimeter wave band at predetermined time intervals; and one or more receiving sections each configured to receive a plurality of reflection signals generated by reflection of the transmission signal on a plurality of persons, and either the biological condition measurement apparatus or the information processing apparatus includes:

a measuring section that measures a plurality of times of flight from the transmission of the transmission signal by the transmitting section until the reception of the plurality of reflection signals by the receiving section; and an identifying section that classifies a plurality of pieces of time-of-flight data representing the plurality of times of flight into a plurality of pieces of time series data including a plurality of pieces of time-of-flight data representing times of flight that fluctuate in a time range equal to or lower than a first threshold, and identifies a biological condition representing motions of an organ of a first person of the plurality of the persons on a basis of a mode of change of times of flight represented by each of the plurality of pieces of time series data, wherein the first threshold is a value that is higher than a maximum value of change amounts of times of flight caused by motions of the organ of the first person, and additionally is smaller than a minimum difference between a time of flight of a reflection signal from the first person and a time of flight of a reflection signal from a second person of the plurality of persons.

* * * * *